(12) United States Patent
Pianca et al.

(10) Patent No.: US 9,248,276 B2
(45) Date of Patent: *Feb. 2, 2016

(54) LEADS WITH SPIRAL OF HELICAL SEGMENTED ELECTRODE ARRAYS AND METHODS OF MAKING AND USING THE LEADS

(71) Applicant: BOSTON SCIENTIFIC NEUROMODULATION CORPORATION, Valencia, CA (US)

(72) Inventors: Anne Margaret Pianca, Santa Monica, CA (US); Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/189,671

(22) Filed: Feb. 25, 2014

(65) Prior Publication Data

US 2014/0180375 A1    Jun. 26, 2014

Related U.S. Application Data

(62) Division of application No. 13/363,059, filed on Jan. 31, 2012, now Pat. No. 8,700,179.

(60) Provisional application No. 61/438,703, filed on Feb. 2, 2011.

(51) Int. Cl.
*A61N 1/05* (2006.01)
*A61N 1/36* (2006.01)
*H05K 13/00* (2006.01)

(52) U.S. Cl.
CPC ............ *A61N 1/0534* (2013.01); *A61N 1/3606* (2013.01); *H05K 13/00* (2013.01); *Y10T 29/49117* (2015.01)

(58) Field of Classification Search
CPC .... A61N 1/05; A61N 1/0534; A61N 1/36182
See application file for complete search history.

(56) References Cited

U.S. PATENT DOCUMENTS 4,602,624 A    7/1986   Naples et al.
4,630,611 A    12/1986  King (Continued)

FOREIGN PATENT DOCUMENTS

EP    0580928 A1    2/1994
EP    0650694 B1    7/1998

(Continued)

OTHER PUBLICATIONS

International Search Report and Written Opinion for International Patent Application No. PCT/US2012/023438 mailed Jun. 8, 2012.

(Continued)

*Primary Examiner* — George Evanisko
(74) *Attorney, Agent, or Firm* — Lowe Graham Jones PLLC; Bruce E. Black

(57) ABSTRACT

A stimulation lead includes a lead body having a longitudinal surface, a distal end, a proximal end, and a shaft extending along at least a portion of the distal end of the lead body. The stimulation lead also includes multiple segmented electrode members disposed on the shaft along the longitudinal surface of the lead body near the distal end of the lead body. Each segmented electrode member includes a ring structure which forms at least a partial ring and is disposed on the shaft, and a segmented electrode coupled to the ring and having an exposed surface configured and arranged for stimulating tissue when the stimulation lead is implanted.

20 Claims, 6 Drawing Sheets

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,016,646 A | 5/1991 | Gotthardt et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,322,559 B1 | 11/2001 | Daulton et al. | |
| 6,510,347 B2 | 1/2003 | Borkan | |
| 6,556,873 B1 | 4/2003 | Smits | |
| 6,564,078 B1 | 5/2003 | Marino et al. | |
| 6,678,564 B2 | 1/2004 | Ketterl et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,203,548 B2 | 4/2007 | Whitehurst et al. | |
| 7,292,890 B2 | 11/2007 | Whitehurst et al. | |
| 7,489,971 B1 | 2/2009 | Franz | |
| 7,668,601 B2 | 2/2010 | Hegland et al. | |
| 7,761,985 B2 | 7/2010 | Hegland et al. | |
| 7,809,446 B2 | 10/2010 | Meadows | |
| 7,822,482 B2 | 10/2010 | Gerber | |
| 7,840,188 B2 | 11/2010 | Kurokawa | |
| 7,848,802 B2 | 12/2010 | Goetz et al. | |
| 7,856,707 B2 | 12/2010 | Cole | |
| 7,860,570 B2 | 12/2010 | Whitehurst et al. | |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,225,504 B2 | 7/2012 | Dye et al. | |
| 8,295,944 B2 | 10/2012 | Howard et al. | |
| 8,321,025 B2 | 11/2012 | Bedenbaugh | |
| 8,473,061 B2 | 6/2013 | Moffitt et al. | |
| 8,560,085 B2 | 10/2013 | Moffitt et al. | |
| 8,583,237 B2 | 11/2013 | Bedenbaugh | |
| 8,649,879 B2 | 2/2014 | DiGiore et al. | |
| 8,862,242 B2 * | 10/2014 | Pianca | 607/115 |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0168805 A1 | 8/2006 | Hegland et al. | |
| 2006/0247697 A1 | 11/2006 | Sharma et al. | |
| 2007/0150036 A1 | 6/2007 | Anderson | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2009/0187222 A1 | 7/2009 | Barker | |
| 2009/0204192 A1 | 8/2009 | Carlton et al. | |
| 2009/0204193 A1 | 8/2009 | Kokones et al. | |
| 2009/0276021 A1 | 11/2009 | Meadows et al. | |
| 2010/0030298 A1 | 2/2010 | Martens et al. | |
| 2010/0036468 A1 | 2/2010 | Decre et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |
| 2010/0094387 A1 | 4/2010 | Pianca et al. | |
| 2010/0100152 A1 | 4/2010 | Martens et al. | |
| 2010/0268298 A1 | 10/2010 | Moffitt et al. | |
| 2010/0269338 A1 | 10/2010 | Dye | |
| 2010/0269339 A1 | 10/2010 | Dye et al. | |
| 2010/0287770 A1 | 11/2010 | Dadd et al. | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0245903 A1 | 10/2011 | Schulte et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2013/0109254 A1 | 5/2013 | Klardie et al. | |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317587 A1 | 11/2013 | Barker | |
| 2013/0325091 A1 | 12/2013 | Pianca et al. | |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | WO-9732628 A1 | 9/1997 |
| WO | WO-9955411 A3 | 2/2000 |
| WO | WO-0038574 A1 | 7/2000 |
| WO | 0158520 A1 | 8/2001 |
| WO | WO-02/068042 A1 | 9/2002 |
| WO | WO-2004045707 A1 | 6/2004 |
| WO | WO-2006083881 A1 | 8/2006 |
| WO | 2008018067 A2 | 2/2008 |
| WO | WO-2008053789 A1 | 5/2008 |
| WO | 2008/100841 A1 | 8/2008 |
| WO | WO-2009025816 A1 | 2/2009 |
| WO | WO-2009102536 A1 | 8/2009 |
| WO | WO-2011005716 A2 | 1/2011 |
| WO | 2013162775 A2 | 10/2013 |
| WO | 2014018092 A1 | 1/2014 |

OTHER PUBLICATIONS

U.S. Appl. No. 12/177,823, filed Jul. 22, 2008.
U.S. Appl. No. 13/951,057, filed Jul. 25, 2013.
U.S. Appl. No. 14/053,112, filed Oct. 14, 2013.
U.S. Appl. No. 14/173,593, filed Feb. 5, 2014.
U.S. Appl. No. 13/363,059, filed Jan. 31, 2012 Official Communication mailed Sep. 24, 2013.
U.S. Appl. No. 14/557,211, filed Dec. 1, 2014.
U.S. Appl. No. 14/286,940, filed May 23, 2014.
U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.
U.S. Appl. No. 14/469,214, filed Aug. 26, 2014.
U.S. Appl. No. 14/286,797, filed May 23, 2014.

* cited by examiner

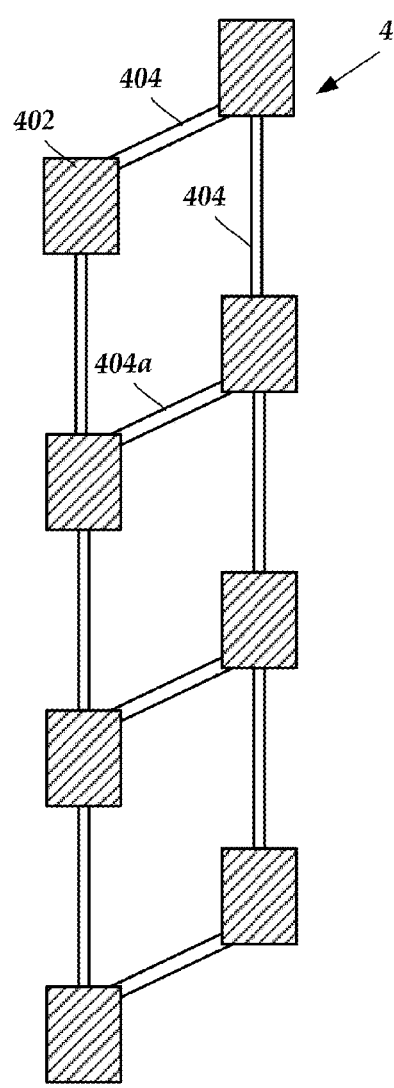
Fig. 4A
Fig. 4B
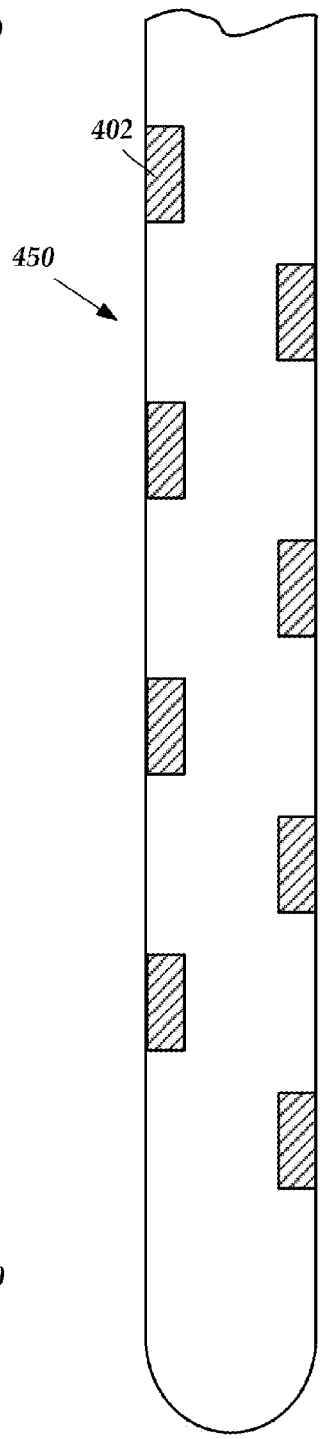
Fig. 4C
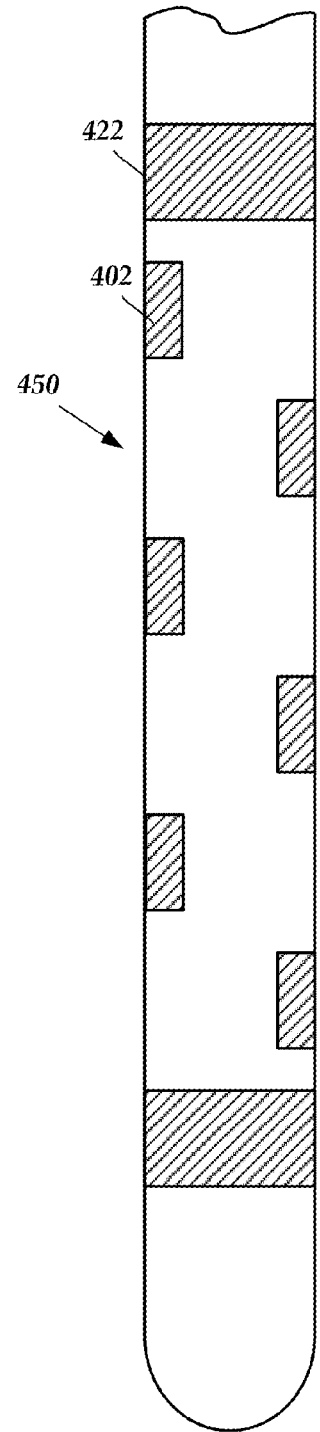
Fig. 4D

LEADS WITH SPIRAL OF HELICAL SEGMENTED ELECTRODE ARRAYS AND METHODS OF MAKING AND USING THE LEADS

CROSS-REFERENCE TO RELATED APPLICATIONS

This application is a divisional application of U.S. patent application Ser. No. 13/363,059 filed Jan. 31, 2012, now allowed, which claims the benefit under 35 U.S.C. §119(e) of U.S. Provisional Patent Application Ser. No. 61/438,703 filed Feb. 2, 2011, all of which are incorporated herein by reference.

FIELD

The invention is directed to the area of electrical stimulation systems and leads and methods of making and using the systems and leads. The present invention is also directed to electrical stimulation leads with segmented electrodes in a spiral, helical, or other arrangement, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead that includes a lead body having a longitudinal surface, a distal end, a proximal end, and a shaft extending along at least a portion of the distal end of the lead body. The stimulation lead also includes multiple segmented electrode members disposed on the shaft along the longitudinal surface of the lead body near the distal end of the lead body. Each segmented electrode member includes a ring structure which forms at least a partial ring and is disposed on the shaft, and a segmented electrode coupled to the ring and having an exposed surface configured and arranged for stimulating tissue when the stimulation lead is implanted.

Another embodiment is a stimulation lead that includes a lead body having a longitudinal surface, a distal end, a proximal end, and an armature extending along at least a portion of the distal end of the lead body. The armature includes at least two arms and defining at least two cutouts between the arms. The stimulation lead further includes multiple keyed electrode members disposed on the armature along the longitudinal surface of the lead body near the distal end of the lead body. Each keyed electrode member includes an electrode disposed in one of the cutouts defined by the armature, and an insulation element which, together with the electrode, forms at least a partial ring around the arms of the armature.

Yet another embodiment is a stimulation lead including a lead body having a longitudinal surface, a distal end, and a proximal end; a ribbon wound within the lead body near the distal end of the lead body; and multiple segmented electrode members disposed on the ribbon. Each segmented electrode member defines a lumen through which the ribbon passes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic top view of one embodiment of a pre-electrode arrangement with segmented electrodes and a scaffold of connector, according to the invention;

FIG. 4B is a schematic side cross-sectional view of the pre-electrode arrangement of FIG. 4A, according to the invention;

FIG. 4C is a schematic side view of one embodiment of a portion of a lead formed using the pre-electrode arrangement of FIG. 4A, according to the invention;

FIG. 4D is a schematic side view of another embodiment of a portion of a lead formed using the pre-electrode arrangement of FIG. 4A, according to the invention;

DETAILED DESCRIPTION

The invention is directed to the area of electrical stimulation systems and leads and methods of making and using the systems and leads. The present invention is also directed to electrical stimulation leads with segmented electrodes in a spiral, helical, or other arrangement, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes. These segmented electrodes can be provided in helical, spiral, or other arrangements to produce directed stimulation current.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Pat. No. 8,473,061 ("Deep Brain Stimulation Current Steering with Split Electrodes"), U.S. Patent Application Publication No. 2009/0187222, and U.S. Patent Application Publication No. 2012/0165911. Each of these references is incorporated herein by reference.

Figure 1:
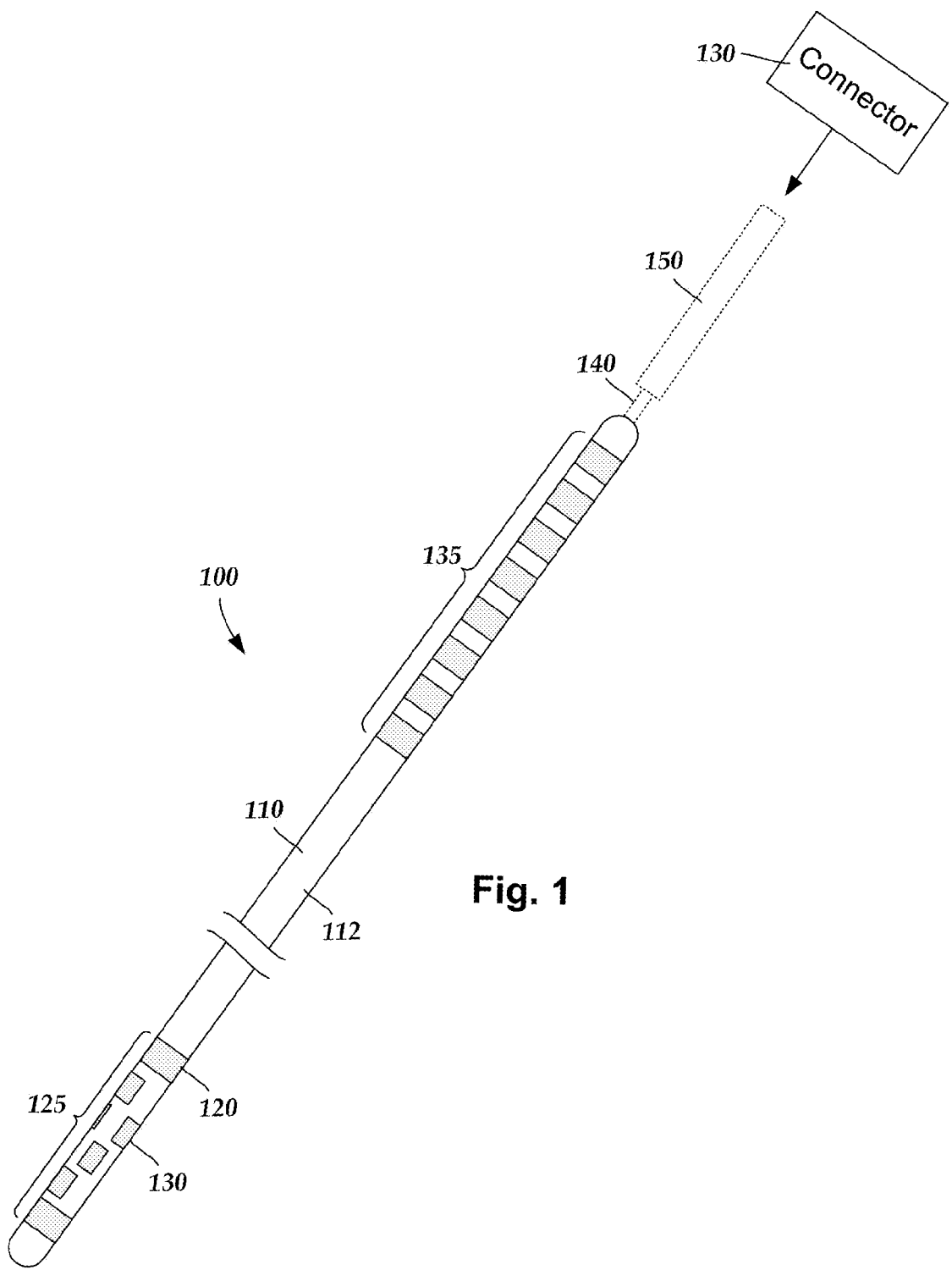
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more, or fewer, than eight stimulation channels (e.g., 4-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). The term "segmented electrode" is used herein to refer to an electrode that does not extend around the entire circumference of the lead (e.g., an electrode that is not a ring electrode). The segmented electrode extends around a portion (i.e., an arc) of the circumference of the lead. In at least some embodiments, the arc may be at least 5, 10, 15, 20, 30, 35, 40, 45, or 60 degrees and, in at least some embodiments, the arc may be no more than 270, 180, 120, 90, 75, 60, 50, 45, 40, 35, 30, 25, or 20 degrees.

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 110 includes a lead body 112, one or more optional ring electrodes 120, and a plurality of sets of segmented electrodes 130. The lead body 112 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 110 may be in contact with body tissue for extended periods of time. In at least some embodiments, the lead 100 has a cross-sectional diameter of no more than 1.5 mm and may be in the range of 1 to 1.5 mm. In at least some embodiments, the lead 110 has a length of at least 10 cm and the length of the lead 110 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 may be optionally disposed on any part of the lead body 112, usually near a distal end of the lead 110. In FIG. 1, the lead 110 includes two ring electrodes 120. Any number of ring electrodes 120 may be disposed along the length of the lead body 112 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 112. In some embodiments, the ring electrodes 120 are substantially cylindrical and wrap around the entire circumference of the lead body 112. In some embodiments, the outer diameters of the ring electrodes 120 are substantially equal to the outer diameter of the lead body 112. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120.

Deep brain stimulation leads may include multiple segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 1, the lead 110 is shown having a plurality of segmented electrodes 130. Any number of segmented electrodes 130 may be disposed on the lead body 112 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 112.

The segmented electrodes 130 may be arranged in any desired configuration. For example, segmented electrodes can be grouped into sets of segmented electrodes, where each set is disposed around a circumference of the lead 110 at a particular longitudinal portion of the lead 110. The lead 110 may have any number segmented electrodes 130 in a given set of segmented electrodes. The lead 110 may have one, two, three, four, five, six, seven, eight, or more segmented electrodes 130 in a given set. In at least some embodiments, each set of segmented electrodes 130 of the lead 110 contains the same number of segmented electrodes 130. The segmented electrodes 130 disposed on the lead 110 may include a different number of electrodes than at least one other set of segmented electrodes 130 disposed on the lead 110.

In some arrangements, the segmented electrodes 130 can be arranged spirally or helically, in one or more spiral or helical paths, on the lead, as illustrated in FIG. 1. Other arrangements of segmented electrodes, including electrodes aligned longitudinally along the surface of the lead or staggered with respect to adjacent electrodes can be used. The pitch of the segmented electrodes (i.e., the longitudinal distance between adjacent electrodes) can be uniform or can vary along the lead.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 110) may be identical in size and shape.

The spacing between individual segmented electrodes may be the same, or different from, the spacing between other segmented electrodes on the lead 110. In at least some embodiments, equal spaces, gaps or cutouts are disposed between each segmented electrode 130 around the circumference of the lead body 112. In other embodiments, the spaces, gaps or cutouts between the segmented electrodes 130 may differ in size or shape. In other embodiments, the spaces, gaps, or cutouts between segmented electrodes 130 may be uniform between the segmented electrodes 130. The segmented electrodes 130 may be positioned in irregular or regular intervals along a length the lead body 112.

Conductor wires (not shown) that attach to the ring electrodes 120 or segmented electrodes 130 extend along the lead body 112. These conductor wires may extend through the material of the lead 110 or along one or more lumens defined by the lead 110, or both. The conductor wires are attached to terminals 135 for coupling of the electrodes 120, 130 to the control unit (not shown).

Figure 2:
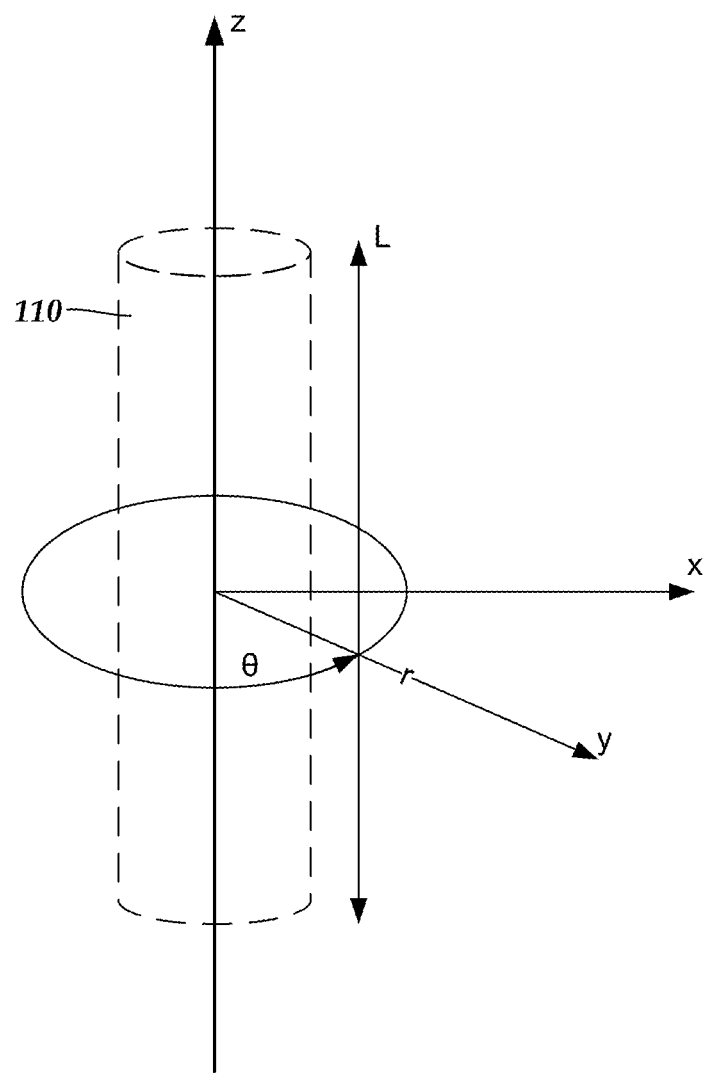
FIG. 2 is a schematic diagram of radial current steering along various electrode levels along the length of a lead, according to the invention.

FIG. 2 is a schematic diagram to illustrate radial current steering along various electrode levels along the length of the lead 110. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 110. In some embodiments, the radial distance, r, and the angle θ around the circumference of the lead 110 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 110.

As can be appreciated from FIG. 2, the centroid of stimulation can be shifted at each level along the length of the lead 110. The use of segmented electrodes at different levels along the length of the lead allows for three-dimensional current steering. In at least some embodiments, each segmented electrode is controlled independently. It will be understood that different stimulation profiles may be produced by varying the arrangement of segmented electrodes along the lead.

The lead can also include recording electrodes or the stimulation electrodes may be used as recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

A variety of different methods and electrode or pre-electrode arrangements can be used to create the segmented electrodes. Moreover, the segmented electrodes can be arranged in a variety of different configurations include spiral or helical arrangements of segmented electrodes.

Figure 3A:
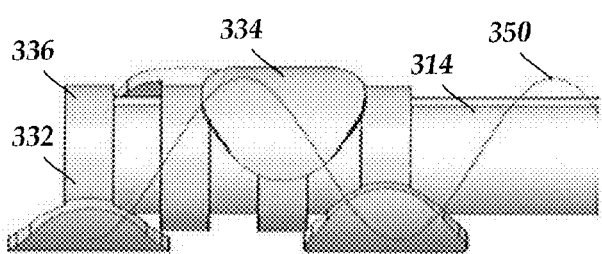
FIG. 3A is a schematic side view of one embodiment of a portion of a lead having a plurality of segmented electrodes arranged in a staggered orientation, according to the invention.
Figure 3C:
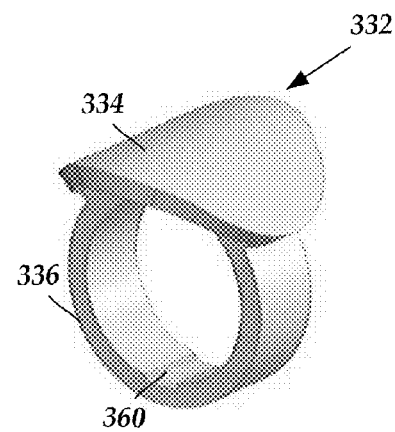
FIG. 3C is a schematic perspective view of one embodiment of segmented electrode member for use in the leads of FIGS. 3A and 3B, according to the invention.
Figure 3B:
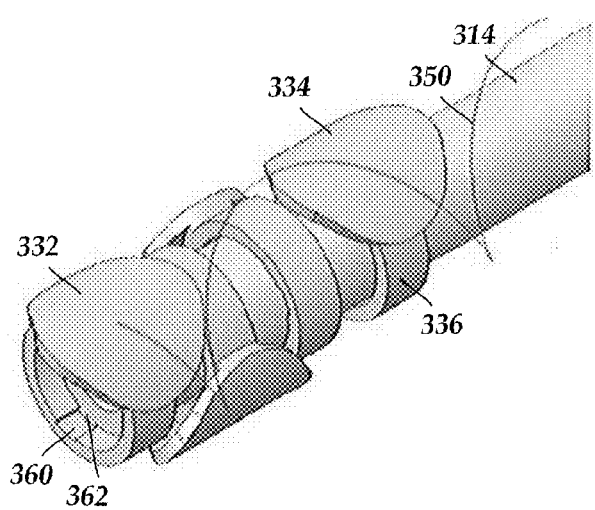
FIG. 3B is a schematic perspective view of one embodiment of a portion of a lead having a plurality of segmented electrodes arranged in a staggered orientation, according to the invention.

FIGS. 3A and 3B illustrate segmented electrode members 332 disposed on a shaft 314 of a lead. Each of the segmented electrode members 332 includes a segmented electrode 334 that is disposed on a ring structure 336 that fits around the shaft. In the completed lead, a non-conductive lead body will be formed over the shaft 314 and ring structures 336 leaving the outer surfaces of the segmented electrodes 334 exposed. Optionally, non-conducting spacers (not shown), such as spacer rings, can be positioned between adjacent segmented electrode members 332 to facilitate maintenance of the spacing between the segmented electrode members.

Figure 3D:
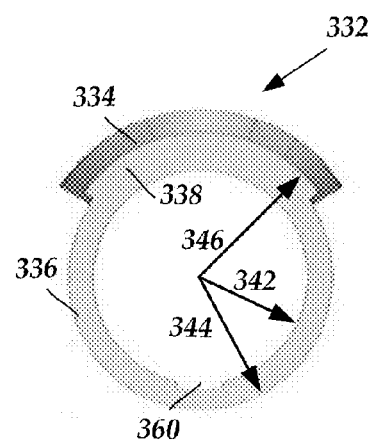
FIG. 3D is a schematic cross-sectional view of the segmented electrode member of FIG. 3C, according to the invention.

FIGS. 3C and 3D illustrate one embodiment of a segmented electrode member 332 with a segmented electrode 334 and a ring structure 336. The outer surface of the segmented electrode 334 is preferably curved with a curvature that matches that of the final lead. The outer surface of the segmented electrode can have any suitable shape including circular, oval, square, rectangular, diamond, hexagonal, octagonal, or any other regular or irregular shape.

The ring structure 336 can be a complete ring (as illustrated in FIGS. 3C and 3D) or a partial ring with a portion cutout (e.g., a C-shaped ring.) In at least some embodiments the ring structure includes a crown portion 338 (FIG. 3D) upon which the segmented electrode 334 sits. The ring structure 336 defines an inner radius 342 (FIG. 3D) which is preferably selected to fit snugly on the shaft 314 and may be equal to or slightly smaller or slightly larger than the outer radius of the shaft to provide an interference fit with the shaft. Away from the crown portion 338, the ring structure 336 also defines an outer radius 344 (FIG. 3D).

The segmented electrode 334 defines an inner radius 346 which may be uniform or vary over the segmented electrode. In at least some embodiments, the inner radius 346 (FIG. 3D) of the segmented electrode 334 at and near at least some edges of the segmented electrode 334, particularly those edges that will be adjacent to, or overlap, the ring structure of another segmented electrode member, is greater than the outer radius 344 of the ring structure 336, as illustrated in FIG. 3D. In other words, at least those portions of the segmented electrode 334 are undercut so that the inner radius 346 of the segmented electrode 334 in those regions is greater than the outer radius 344 of the ring structure 336. Such an arrangement will prevent conductive contact between the segmented electrode of one member with the ring structure of another member (see, for example, FIGS. 3A and 3B).

Figure 3E:
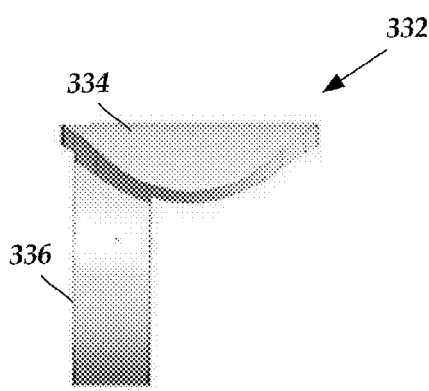
FIG. 3E is a schematic side view of one embodiment of a segmented electrode member with a ring structure attached to the edge of the segmented electrode, according to the invention.
Figure 3F:
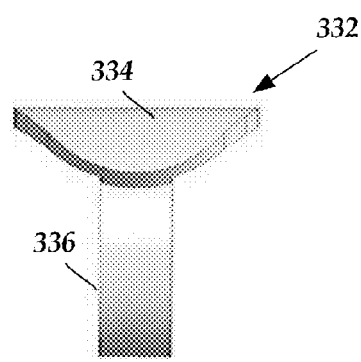
FIG. 3F is a schematic side view of one embodiment of a segmented electrode member with a ring structure attached to the center of the segmented electrode, according to the invention.

The ring structure 336 can be attached to the segmented electrode 334 at the center of the segmented electrode 334, as illustrated in FIG. 3F, or at an edge of the segmented electrode 334, as illustrated in FIG. 3E, or anywhere between the center and the edge of the segmented electrode. The longitudinal length (i.e., the length parallel to the longitudinal axis of the lead) of the ring structure 336 is smaller than the longitudinal length of the segmented electrode 334 as illustrated in FIGS. 3E and 3F.

The segmented electrode member 332 can be formed using a metal, alloy, conductive oxide, or any other suitable conductive biocompatible electrode material. In some embodiments, the ring structure 336 or a portion of the ring structure may be formed of a non-conductive material. The segmented electrode 334 and ring structure 336, or portions of these components, can be made using the same material or different materials. The ring structure 336 and segmented electrode 334 can be formed using a single piece of metal or these components can be formed as separate pieces and joined together using any suitable method (for example, welding, soldering, crimping, adhesive binding, and the like).

A conductor (not shown), which may be carried within the shaft 314 and which is attached to a terminal on the proximal end of the lead, can be attached to any conductive portion of the segmented electrode member 332 that is in electrical communication with the segmented electrode 334. For example, the conductor can be attached (e.g., welded, soldered, or otherwise attached) to a portion of the interior surface of the ring structure 336. This arrangement electrically couples the segmented electrode 334 to a terminal at the proximal end of the lead.

In at least some embodiments, the segmented electrode member 332 and shaft 314 have complementary groove 360 and key 362 structures. In the illustrated embodiments, the segmented electrode members 332 have grooves 360 and the shaft 314 defines the corresponding key 362, but the opposite arrangement (a groove on the shaft and keys on the segmented electrode members) could also be used. The groove and key structures facilitate positioning the segmented electrode members 332 on the shaft 314 and retaining the segmented electrode members in their desired position by hindering rotation of the segmented electrode members around the shaft. It will be recognized that the position of the groove 360 (or key 362) on the segmented electrode member need not be the same for each of the segmented electrode members 332. For example, in at least some embodiments, the groove 360 (or key 362) is provided at different positions for each of the segmented electrode members so that the segmented electrode members can be aligned in different orientations on a shaft with a single key (or groove), as illustrated in FIGS. 3A and 3B. As an alternative, the segmented electrode members may include multiple grooves (or keys) and a manufacturer may choose one of the grooves (or keys) to provide a desired orientation of the particular segmented electrode member on the shaft.

As indicated above, a portion of the lead body is formed over the shaft 314 and ring structures 336 leaving at least the outer surface of the segmented electrodes 334 exposed. The resulting arrangement can be, for example, the lead of FIG. 1. Any suitable method for forming the lead body over the shaft and ring structures can be used including, but not limited to, molding the lead body around the shaft and ring structures or disposing a polymer tube over the shaft and segmented electrode members and reflowing the polymer tube to form the lead body. In some embodiments, the outer surfaces of the segmented electrodes 334 are isodiametric with the lead body. In other embodiments, the outer surfaces of the segmented electrodes 334 may extend beyond the lead body or be recessed from the outer surface of the lead body (but still exposed to tissue when implanted).

The segmented electrodes 334 may be arranged in any desired configuration including, but not limited to, spiral or helical arrangements such as those illustrated in FIGS. 3A and 3B. For example, the curve 350 in FIGS. 3A and 3B shows the helical or spherical arrangement of the segmented electrodes 334. In some embodiments, adjacent or non-adjacent segmented electrodes may be aligned along the longitudinal axis of the lead. In other embodiments, none of the segmented electrodes is aligned longitudinally. It will also be recognized that, in addition to the segmented electrodes, a lead may also include one or more ring electrodes (see, for example, FIG. 1) and that any relative arrangement of ring electrodes and segmented electrodes may be used.

FIGS. 3A and 3B illustrate arrangements in which the segmented electrodes form a spiral or helical pattern with uniform pitch (i.e., uniform distance between electrodes). It will be recognized that in other embodiments that pitch of some or all of the segmented electrodes may vary along the length of the lead. For example, the pitch may increase or decrease or there may be portions that where the pitch increases and portions where the pitch decreases along the length of the lead. There also may be portions where the pitch remains the same. It will also be recognized that the segmented electrodes may form more than one helix or spiral. For example, the segmented electrodes may be disposed in a double helix around the lead. The number of segmented electrodes in a full turn of the helix or spiral can be two, three, four, or more (and may even be a non-integer number) and may be the same or different for each turn of the helix or spiral. It will also be recognized the segmented electrode members can be formed in other patterns including linear arrangements of segmented electrodes.

Another method of making a lead with segmented electrodes in a spiral or helical arrangement includes forming a pre-electrode assembly with electrodes connected together by a scaffold with raised connectors. Preferably, the pre-electrode assembly is a metal assembly with metal electrodes and metal connectors that couple the electrodes to each other. Preferably, the electrodes and connectors are formed from a single sheet of metal. Examples of other pre-electrode assemblies with different arrangements of electrodes and connectors, and techniques for forming a lead that can be applied to the present pre-electrode assemblies, can be found in U.S. Patent Application Publication No. 2012/0165911, incorporated herein by reference.

FIGS. 4A and 4B illustrate one embodiment of a pre-electrode assembly 400 with electrodes 402 and a scaffold of raised connectors 404. Each electrode 402 is directly coupled to at least one other electrode by at least one, two, or three of the raised connectors 404. Preferably, the electrodes 402 and raised connectors 404 are aligned to provide a spiral or helical arrangement when wrapped on a lead. In some embodiments, the electrodes may be arranged in longitudinal columns. The exposed outer surface of the electrodes 402 is preferably curved with a curvature that matches that of the final lead. The exposed outer surface of the electrodes 402 can have any suitable shape including circular, oval, square, rectangular, diamond, hexagonal, octagonal, or any other regular or irregular shape.

The scaffold of connectors 404 is preferably arranged, as illustrated in FIG. 4A, to produce the spiral or helical arrangement of the electrodes. For example, at least some of the connectors (e.g., connector 404a) are angled with respect to the electrodes to facilitate spiral or helical alignment of the electrodes. The angle of these connectors, with respect to an edge of the electrode to which the connector is attached, is at least 5 degrees and less than 85 degrees. The angle may be in the range of 10 to 80 degrees or in the range of 15 to 75 degrees or in the range of 20 to 70 degrees or in the range of 30 to 60 degrees. Although FIGS. 4A and 4B illustrate electrodes coupled to other electrodes using a single connector between any two electrodes, it will be understood that multiple connectors can be used between any two electrodes.

The raised connectors 404 are provided to hold the electrodes 402 in alignment during the manufacture of the lead and will be removed during manufacture as described below. Preferably, the electrodes 402 and connectors 404 are made of the same material. In at least some embodiments, the electrodes 402 and connectors 404 are formed from a single sheet of metal. Preferably, the pre-electrode assembly includes gaps between the electrodes 402 and connectors 404. Preferably, the connectors 404 are raised above the electrodes 402 by an amount greater than a thickness of the connectors 404, as illustrated in FIG. 4B, and may be raised at least twice, three times, four times, or ten times the thickness of the connectors 404. This can facilitate removal of the connectors later in the process of manufacturing.

The connectors 404 can be any suitable size, width, length, and thickness. The length of the connectors 404 is the separation distance between the two electrodes coupled by the connector. The width and thickness can be selected to provide a desired amount of stability when maintaining the electrodes in the desired arrangement. It will be recognized that this factor is counterbalanced by the additional effort in forming a tube (see below) with a pre-electrode assembly with wider or thicker connectors; as well as the additional amount of material that will be removed with removal of the connectors. In some embodiments, the width of the connector is no more than half, one-third, or one-quarter of the length of the connector. It will be recognized that the width and thickness of each of the connectors can be uniform or can vary along the length of the connectors. It will also be recognized that the connectors may have the same lengths, widths, and thicknesses or there may be variation in these parameters between connectors.

The pre-electrode assembly 400 with electrodes 402 and connectors 404 can be formed by any suitable method. For example, the pre-electrode assembly 400 can be formed by stamping a sheet of metal or other conductive material or by machining or molding metal or other conductive material into the desired shape. Preferably, the stamping or molding of the pre-electrode assembly 400 results in the connectors 404 being raised with respect to the electrodes, as illustrated in FIG. 4B. If not, the connectors 404 can be raised in a separate step by, for example, stamping (e.g., a second stamping step) or otherwise bending the pre-electrode assembly to form the raised connectors. The gaps between electrodes and between connectors may be formed when the pre-electrode assembly is formed by stamping or molding. Alternatively or additionally, some or all of the gaps may be formed prior to stamping or after stamping or molding; for example, the gaps may be formed by stamping, cutting, and the like.

Optionally, the electrodes 402 can include tabs (not shown) that may be folded down during manufacture to interlock the electrodes with the material of the lead body described below. The tabs can protrude into the lead body and provide an anchoring mechanism to prevent dislodgment of the individual electrode segments.

In forming the lead, the pre-electrode assembly 400 is formed into a tube. In at least some embodiments, the pre-electrode assembly 400 is wrapped around a mandrel, a shaft, or other cylindrical element to facilitate formation of the tube. In one embodiment the pre-electrode assembly 400 is wrapped around a shaft that includes a central lumen and optionally one or more conductor lumens. The tube formed by the pre-electrode assembly can have any suitable shape including, but not limited to, tubes with circular, square, rectangular, oval, triangular, hexagonal, or octagonal cross-sections. In another embodiment, the pre-electrode assembly can be formed or rolled into a cylinder.

The tube formed by the pre-electrode assembly defines a longitudinal axis along the tube. Preferably, each of the raised connectors is disposed at a radius with respect to the longitudinal axis that is greater than a radius of any of the electrodes.

The pre-electrode assembly can be held in the cylindrical form by any suitable method. For example, straps or fasteners may be attached to the pre-electrode assembly, or wrapped around the pre-electrode assembly, to hold it in the cylindrical form. Alternatively or additionally, two or more portions of the pre-electrode assembly may overlap and the overlapping regions of the carrier can be attached to each other by welding, soldering, application of adhesive, or the like. In other embodiments, the forming process will cause the metal to yield and hence the material will take a permanent change in shape by, for example, deformation of the material.

In at least some embodiments, conductor wires (not shown) are attached to the individual electrodes 402 before or after forming the pre-electrode assembly into a tube. The conductor wires can be, for example, insulated wires with a portion of the insulation removed to make contact with the electrodes 402. A different conductor wire can be attached to each electrode 402. In other embodiments, the same conductor wire may be attached to two or more of the electrodes.

The conductor wires can be attached by any suitable method including, but not limited to, welding, soldering, crimping, staking, using a conductive adhesive, and the like. The conductor wires can be attached to any suitable part of the electrodes 402. In some embodiments, the conductor wires are disposed in conductor lumens in a shaft or other portion of the lead. One or more conductor wires may be disposed in each conductor lumen. In at least some embodiments, each conductor lumen has a single conductor wire disposed therein. Portions of the conductor lumens can be exposed (e.g., by ablating or removing a portion of the lead tube) to provide access for attachment of the conductor wire to the electrode.

A portion of the lead body is then formed around the pre-electrode assembly. Preferably a portion of the lead body is formed beneath the connectors 404. Preferably, the portion of the lead body that is formed is capable of retaining the electrodes 402 within the lead and in the desired orientation and configuration after removal of the connectors, as described below. Optionally, the formation of the lead body may also incorporate other electrodes, such as ring electrodes 422 (see FIG. 4D), into the structure of the lead. In some embodiments, the portion of the lead body may incorporate pre-existing structures, such as the lead tube, into the lead body during its formation.

The portion of the lead body can be formed by any suitable method including, but not limited to, molding the portion of the lead body around the pre-electrode assembly. As another example, polymeric material, such as polymer tubing (e.g., polyurethane or silicone tubing), may be placed over the pre-electrode assembly and then heated to allow the material of the polymer tubing to reflow and form the portion of the lead body. In some embodiments, a heat shrink tube may be temporarily placed over the polymer tubing, prior to reflow, so that the material of the polymer tubing is retained during reflow. The heat shrink tubing may then be removed (e.g., cut off) after reflow of the polymer tubing.

The connectors are then removed by grinding or any other suitable method. For example, the pre-electrode assembly can be ground down to the level of the dotted line 460 in FIG. 4B. FIGS. 4C and 4D illustrate embodiments of a lead 450 after removal of the connectors. In some embodiments, the connectors are removed by centerless grinding. Optionally, the grinding may also remove portions of the lead body, the electrodes, or both. In at least some embodiments, the grinding provides a lead that is isodiametric at the distal end or along the entire lead.

Figure 5A:
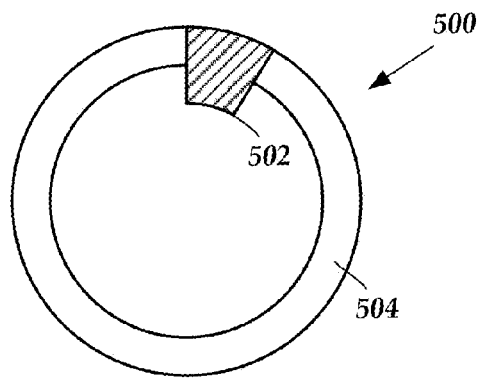
FIG. 5A is a schematic cross-sectional view of one embodiment of a keyed electrode member, according to the invention.
Figure 5B:
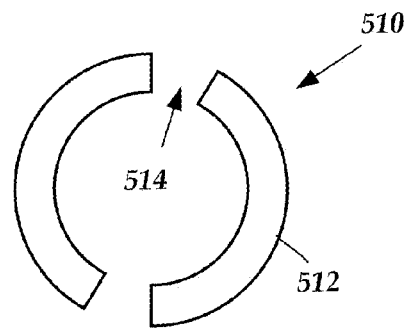
FIG. 5B is a schematic cross-sectional view of one embodiment of an armature, according to the invention.
Figure 5C:
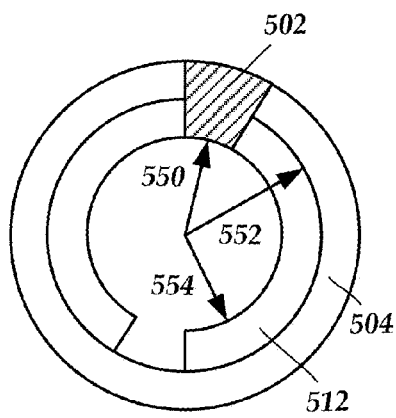
FIG. 5C is a schematic cross-sectional view of the combination of the keyed electrode member of FIG. 5A and armature of FIG. 5B, according to the invention.

Another method for forming a lead with segmented electrodes, such as that illustrated in FIG. 1, uses keyed electrodes and an armature assembly in the lead body. FIG. 5A is a cross-sectional illustration of a keyed electrode member 500 that includes an electrode 502 and an insulation element 504 that together form a ring. FIG. 5B is a cross-sectional illustration of an armature 510 that is disposed at the distal end of the lead during manufacture. The armature 510 includes at least two arms 512 and at least two cutouts 514 between the arms into which the electrode 502 will fit. FIG. 5C illustrates the keyed electrode member 500 slid onto the armature 510 with the electrode 502 fit into one of the cutouts 514.

The electrode 502 can be made of any suitable biocompatible electrode conductive material. An inner radius 550 of the electrode 502, defined as the distance from the center of the lead to the innermost part of the electrode, is preferably smaller than an inner radius 552 of the insulation element 504. An inner radius 550 of the electrode 502 may be equal to, larger than, or smaller than, an inner radius 554 of the armature. The electrode 502 is attached to a conductor (not shown) that is coupled to one of the terminals at the proximal end of the lead. The electrode 502 can be attached to the conductor prior to, or after, sliding the electrode onto the armature 510. The exposed outer surface of the electrodes 502 is preferably curved with a curvature that matches that of the final lead. The exposed outer surface of the electrodes 502 can have any suitable border shape including circular, oval, square, rectangular, diamond, hexagonal, octagonal, or any other regular or irregular shape.

The insulation element 504 may be made of any suitable biocompatible non-conductive material including any of the materials described above for use as the lead body. The insulation element 504, with the electrode 502, can form a complete ring or the can form a partial ring (for example, a "C"-shaped ring) with a slit. Preferably, the inner radius 552 of the insulation element is equal to or slightly less than the outer radius of the armature. The insulation element 504 is coupled to the electrode 502 including, but not limited to, adhesive, a portion of the insulation element extending through a lumen in the electrode, and the like.

The armature 510 can be made of any suitable biocompatible non-conductive material. The armature 510 may include two, three, four, five, or more arms and may include two, three, four, five, or more cutouts. The arms and cutouts can be spaced uniformly or non-uniformly. Optionally, the arms may define lumens through which one or more conductors may pass. The conductors can be used to couple the electrodes 502 to terminals at the proximal end of the lead. The armature can be formed by any suitable method including, for example, molding or extruding the arms or by laser ablating a tubular shaft of the lead.

After disposing the keyed electrode member 500 on the armature, a non-conductive spacer 516 (FIG. 5E) can then be slid onto the armature. The spacer 516 may be made of any suitable biocompatible non-conductive material including any of the materials described above for use as the lead body.

Figure 5D:
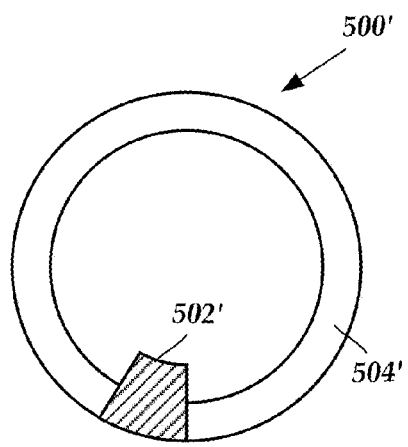
FIG. 5D is a schematic cross-sectional view of another embodiment of a keyed electrode member, according to the invention.
Figure 5E:
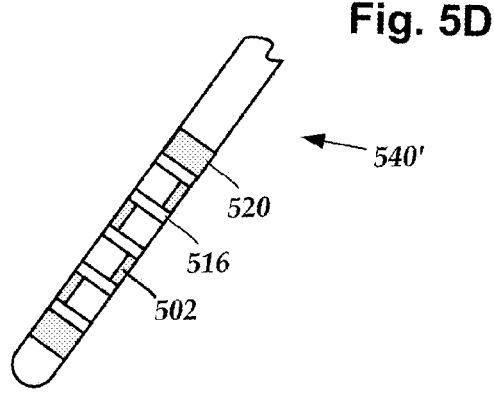
FIG. 5E is a schematic side view of one embodiment of a portion of a lead formed using the keyed electrode member of FIG. 5A, the armature of FIG. 5B, and the keyed electrode member of FIG. 5D, according to the invention.

After the spacer 516, a second keyed electrode member 500', as illustrated in FIG. 5D, can be slid onto the armature, followed by another spacer. This can be repeated as desired to form an arrangement of electrodes. In the instances, where the armature includes two cutouts, the electrodes can alternate between the cutouts. When the armature includes more than two cutouts, the electrodes can be arranged in the respective cutouts in a clockwise or counterclockwise manner or any other desired arrangement.

One example of an arrangement of electrodes on a distal end of lead 540' is illustrated in FIG. 5F. This example also includes optional ring electrodes 520 which may be slid onto the armature as well. In at least some embodiments, the spacers 516 and insulation elements 504 (and possibly the arms 512 of the armature) may be reflowed after arranging the electrodes 502 on the lead to facilitate maintaining the electrodes in the desired positions and orientations. The electrodes may include a through hole or other element that can receive a portion of the reflowed material or may include a roughed surface. Such features can facilitate maintaining the position and orientation of the segmented electrodes within the lead.

This method of arranging the electrodes on the lead can be used to generate spiral or helical or other desired electrodes arrangements. These arrangements may have uniform or varying pitch. Pitch may be varied by, for example, varying the width of the spacers 516.

Figure 6A:
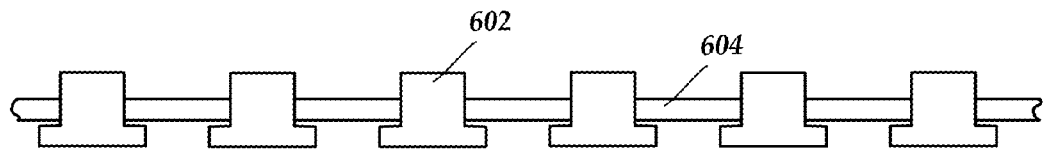
FIG. 6A is a schematic side view of one embodiment of a ribbon with segmented electrodes, according to the invention.

Segmented electrodes can also be positioned on a ribbon and wrapped around a shaft to form a segmented electrode lead. FIG. 6A illustrates one embodiment of segmented electrodes 602 disposed on a non-conductive ribbon 604. The ribbon 604 can be made of any suitable material including, but not limited to, polyurethane, silicone, polytetrafluoroethylene (e.g., Teflon™), or the like. The ribbon may be a monofilament. The ribbon may have any suitable cross-sectional shape including, but not limited to, circular, oval, rectangular, square, or the like. The electrodes 602 can be positioned at regular or irregular distances along the ribbon 604. The ribbon may include knots or other features or adhesive, clips, or the like may be placed on the ribbon to facilitate maintenance of the position of the electrodes on the ribbon.

Figure 6B:
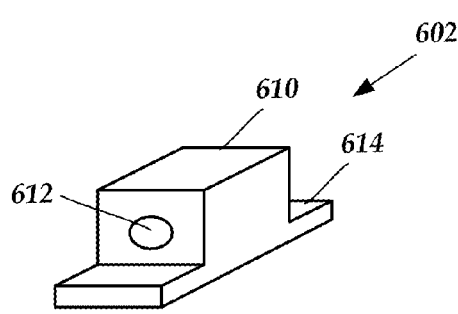
FIG. 6B is a schematic perspective view of one embodiment of a segmented electrode for use in the arrangement of FIG. 6A, according to the invention.

FIG. 6B is a perspective view of one of the segmented electrodes 602. Each segmented electrode 602 includes a body 610 and a lumen 612 through which the ribbon 604 (not shown) is passed. Optionally, the segmented electrode includes one or more tabs 614 that extend outward from the body 610. In the lead, these tabs will be covered by a portion of the lead body and facilitate maintenance of the segmented electrode within the lead, as well as maintenance of the relative position of the segmented electrode on the lead. The segmented electrode 614 can be formed of any suitable biocompatible conductive material. It will be understood that the segmented electrodes 602 of a lead may be the same or the segmented electrodes may be different in size, shape, materials, and the like. The exposed outer surface of the electrodes 602 is preferably curved with a curvature that matches that of the final lead. The exposed outer surface of the electrodes 602 can have any suitable shape including circular, oval, square, rectangular, diamond, hexagonal, octagonal, or any other regular or irregular shape.

Figure 6C:
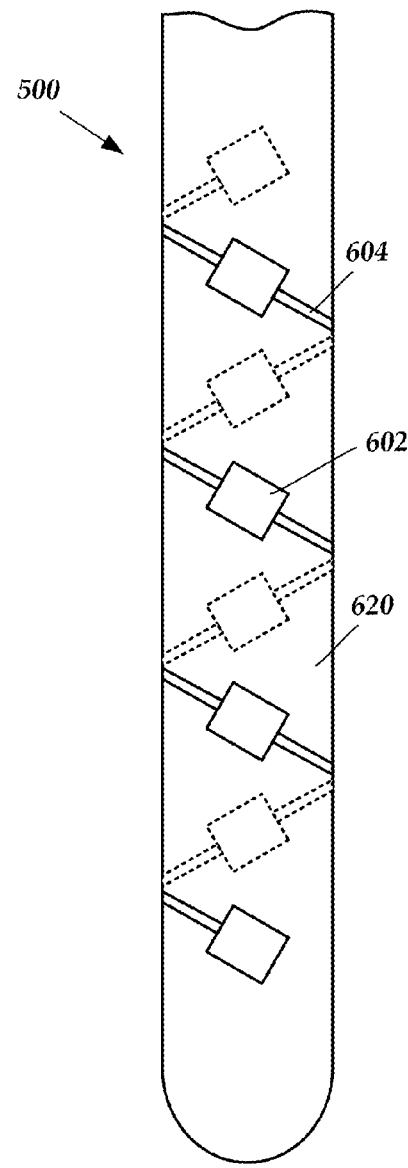
FIG. 6C is a schematic side view of one embodiment of the ribbon with segmented electrodes of FIG. 6A wrapped around a shaft for forming a lead, according to the invention.

FIG. 6C illustrates the segmented electrodes 602 and ribbon 604 wrapped around a shaft 620 of a lead (segmented electrodes 602 and portions of the ribbon 604 that are on the back side of the shaft 620 are indicated by dotted lines). The segmented electrodes/ribbon can be wrapped around the shaft in any suitable arrangement. FIG. 6C illustrates one arrangement in which the segmented electrodes form a spiral or helical pattern with uniform pitch (i.e., uniform distance between electrodes). It will be recognized that in other embodiments that pitch of some or all of the segmented electrodes may vary along the length of the lead. For example, the pitch may increase or decrease or there may be portions that where the pitch increases and portions where the pitch decreases along the length of the lead. There also may be portions where the pitch remains the same. It will also be recognized that more than one segmented electrodes/ribbon arrangement can be wrapped around the shaft. For example, two segmented electrodes/ribbon arrangement can be wrapped in a double-helix arrangement. As another example, two or more segmented electrodes/ribbon arrangements can be wrapped consecutively around to the shaft to form a longer longitudinal arrangement of segmented electrodes.

The segmented electrodes 602 are attached to conductors (not shown) that are coupled to one or more terminals at the proximal end of the lead. The conductors may be attached prior to, or after, wrapping the segmented electrodes/ribbon around the shaft.

A portion of the lead body is then formed around the wrapped segmented electrodes/ribbon. Preferably a portion of the lead body is formed over the ribbon 604 and the optional tabs 614. Preferably, the portion of the lead body that is formed is capable of retaining the electrodes 602 within the lead and in the desired orientation and configuration after removal of the connectors, as described below. Optionally, the formation of the lead body may also incorporate other electrodes, such as ring electrodes (not shown), disposed on the shaft.

The portion of the lead body can be formed by any suitable method including, but not limited to, molding the portion of the lead body around the shaft, segmented electrodes, and ribbon. As another example, polymeric material, such as polymer tubing (e.g., polyurethane or silicone tubing), may be placed over the shaft, segmented electrodes, and ribbon and then heated to allow the material of the polymer tubing to reflow and form the portion of the lead body. In some embodiments, the ribbon may also reflow and optionally mix with the lead body. In some embodiments, a heat shrink tube may be temporarily placed over the polymer tubing, prior to reflow, so that the material of the polymer tubing is retained during reflow. The heat shrink tubing may then be removed (e.g., cut off) after reflow of the polymer tubing. In some embodiments, the lead may be ground (e.g., using centerless grinding) to remove excess insulation and ensure that the top surface of the segmented electrodes is exposed.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent Of the United States is:

1. An assembly for forming a stimulation lead, comprising:
a lead body having a distal end and a proximal end; and
a pre-electrode assembly formed in a tube around a portion of the distal end of the lead body and comprising a plurality of segmented electrodes and a plurality of raised connectors, wherein the segmented electrodes form at least one helix or spiral, wherein each of the segmented electrodes is coupled to at least one other of the segmented electrodes by at least one of the raised connectors and the segmented electrodes and the raised connectors are formed of a same conductive material, the tube defining a longitudinal axis, wherein each of the raised connectors is disposed at a radius with respect to the longitudinal axis that is greater than a radius of any of the segmented electrodes with respect to the longitudinal axis, wherein each of the segmented electrodes is attached to one of the raised connectors at an angle in a range of 10 to 80 degrees with respect to an edge of that segmented electrode.

2. The assembly of claim 1, further comprising at least one ring electrode disposed around a portion of the distal end of the lead body.

3. The assembly of claim 1, wherein the segmented electrodes of the pre-electrode assembly form a single helix.

4. The assembly of claim 1, wherein the segmented electrodes of the pre-electrode assembly form a double helix.

5. The assembly of claim 1, wherein each of the segmented electrodes is directly coupled to at least two other of the segmented electrodes by the raised connectors.

6. The assembly of claim 1, wherein the angle is in a range of 30 to 60 degrees.

7. A method of making a stimulation lead, the method comprising:
forming the assembly of claim 1 by:
providing a pre-electrode assembly comprising the plurality of segmented electrodes and the plurality of raised connectors,
forming the pre-electrode assembly into the tube with the segmented electrodes forming at least one helix or spiral; and
forming at least a portion of the lead body around the segmented electrodes of the pre-electrode assembly; and
grinding the tube comprising the pre-electrode assembly and portion of the lead body to remove the plurality of raised connectors leaving the plurality of segmented electrodes and the portion of the lead body.

8. The method of claim 7, wherein the angle is in a range of 20 to 70 degrees.

9. The method of claim 7, wherein providing a pre-electrode assembly comprises stamping a metal sheet to form the plurality of segmented electrodes and the plurality of raised connectors.

10. The method of claim 9, wherein stamping the metal sheet comprises forming a plurality of gaps between the segmented electrodes and the raised connectors.

11. The method of claim 9, wherein stamping the metal sheet comprises stamping the metal sheet to form the plurality of segmented electrodes and a plurality of connectors and then bending the plurality of connectors to form the plurality of raised connectors.

12. The method of claim 7, wherein forming the pre-electrode assembly into the tube comprises wrapping the pre-electrode assembly around a cylindrical shaft.

13. The method of claim 12, wherein wrapping the pre-electrode assembly comprises wrapping the pre-electrode assembly around a lead tube defining at least one lumen through the lead tube.

14. The method of claim 7, further comprising attaching a conductor wire to at least one of the electrodes prior to forming the pre-electrode assembly into the tube.

15. The method of claim 7, further comprising attaching a conductor wire to at least one of the electrodes after forming the pre-electrode assembly into the tube.

16. The method of claim 7, wherein forming the portion of the lead body comprises molding the portion of the lead body around the segmented electrodes.

17. The method of claim 7, wherein forming the portion of the lead body comprises forming polymeric material beneath the connectors.

18. The method of claim 7, wherein grinding the tube comprises grinding the tube comprising the pre-electrode assembly and the portion of the lead body to form an isodiametric lead.

19. The method of claim 7, wherein the segmented electrodes of the pre-electrode assembly form a single helix.

20. The method of claim 7, wherein the segmented electrodes of the pre-electrode assembly form a double helix.

* * * * *